(12) United States Patent
Jones, Jr.

(10) Patent No.: US 8,272,280 B2
(45) Date of Patent: Sep. 25, 2012

(54) APPARATUS AND METHOD OF CONTAMINANT DETECTION FOR FOOD INDUSTRY

(76) Inventor: Arthur T. Jones, Jr., Houston, TX (US)

( * ) Notice: Subject to any disclaimer, the term of this patent is extended or adjusted under 35 U.S.C. 154(b) by 40 days.

(21) Appl. No.: 12/947,625

(22) Filed: Nov. 16, 2010

(65) Prior Publication Data

US 2011/0065097 A1 Mar. 17, 2011

Related U.S. Application Data

(63) Continuation of application No. 10/999,319, filed on Nov. 29, 2004, now Pat. No. 7,905,154.

(51) Int. Cl.
*G01N 1/24* (2006.01)
*G01N 21/94* (2006.01)

(52) U.S. Cl. ............ 73/864.81; 73/23.34; 73/31.02; 73/31.03; 73/31.05; 73/863.21

(58) Field of Classification Search ............. 73/865.8, 73/23.34, 31.01, 31.02, 31.05, 23.42, 23.41; 426/231
See application file for complete search history.

(56) References Cited

U.S. PATENT DOCUMENTS

| | | | | |
|---|---|---|---|---|
| 1,538,369 A * | 5/1925 | Akiyama | ............ | 426/319 |
| 1,703,468 A * | 2/1929 | Biesen | ............ | 165/108 |
| 2,169,081 A * | 8/1939 | James | ............ | 426/55 |
| 2,339,507 A * | 1/1944 | Nagy et al. | ............ | 426/55 |
| 2,524,182 A * | 10/1950 | Teigen | ............ | 426/331 |
| 2,834,188 A * | 5/1958 | Bradford | ............ | 62/91 |
| 3,025,170 A * | 3/1962 | Murphy et al. | ............ | 426/332 |
| 3,238,556 A * | 3/1966 | Martin | ............ | 15/330 |
| 3,255,599 A * | 6/1966 | Morrison | ............ | 62/63 |
| 3,304,733 A * | 2/1967 | Coffman | ............ | 62/100 |
| 3,421,836 A * | 1/1969 | Caplan et al. | ............ | 422/4 |
| 3,479,688 A * | 11/1969 | Hoersch | ............ | 452/52 |
| 3,523,891 A * | 8/1970 | Mehl | ............ | 210/707 |
| 3,546,114 A * | 12/1970 | Moller, Jr. et al. | ............ | 210/760 |
| 3,549,528 A * | 12/1970 | Armstrong | ............ | 210/760 |
| 3,613,386 A * | 10/1971 | Klee | ............ | 62/64 |
| 3,637,405 A * | 1/1972 | Mendelson et al. | ............ | 426/2 |
| 3,689,958 A * | 9/1972 | Dillon | ............ | 99/517 |
| 3,709,142 A * | 1/1973 | Peterson | ............ | 99/357 |
| 3,715,891 A * | 2/1973 | Martin | ............ | 62/63 |
| 3,729,773 A * | 5/1973 | Dillon | ............ | 426/524 |
| 3,743,523 A * | 7/1973 | Bodine | ............ | 426/238 |

(Continued)

FOREIGN PATENT DOCUMENTS

DE 19806041 A1 * 8/1999

(Continued)

OTHER PUBLICATIONS

Perkins, Sid, Eau Brother!—Electronic Noses Provide a New Sence of the Future, Feb. 19, 2000, Science News, vol. 157, No. 8, pp. 125.*

(Continued)

*Primary Examiner* — David Rogers
(74) *Attorney, Agent, or Firm* — David McEwing, PC

(57) ABSTRACT

The present invention is a method and apparatus for contaminant detection in the food industry. Particularly, the method and apparatus involve collecting air samples containing aerosolized contaminate particles from a foodstuff and analyzing the sample for presence of a contaminate. Aerosol lab-on-a-chip and/or electronic nose devices are utilized for the detection of contaminant particles.

20 Claims, 9 Drawing Sheets

U.S. PATENT DOCUMENTS

| | | | | |
|---|---|---|---|---|
| 3,745,026 | A * | 7/1973 | Hansen et al. | 26/332 |
| 3,748,905 | A * | 7/1973 | Fletcher et al. | 73/863.25 |
| 3,769,807 | A * | 11/1973 | Foster | 62/63 |
| 3,958,026 | A * | 5/1976 | Leone et al. | 426/332 |
| 4,021,585 | A * | 5/1977 | Svoboda et al. | 426/332 |
| 4,171,625 | A * | 10/1979 | Morgan et al. | 62/380 |
| 4,180,592 | A * | 12/1979 | Buckley et al. | 426/32 |
| 4,196,221 | A * | 4/1980 | Dew | 426/235 |
| 4,245,483 | A * | 1/1981 | Murai | 62/376 |
| 4,309,388 | A * | 1/1982 | Tenney et al. | 422/304 |
| 4,309,795 | A * | 1/1982 | Simonsen | 452/76 |
| 4,325,221 | A * | 4/1982 | Grewar | 62/63 |
| 4,367,630 | A * | 1/1983 | Bernard et al. | 62/63 |
| 4,403,479 | A * | 9/1983 | Rasovich | 62/63 |
| 4,477,357 | A * | 10/1984 | Sittenfield | 210/748.04 |
| 4,484,517 | A * | 11/1984 | Amann | 99/474 |
| 4,517,159 | A * | 5/1985 | Karlson | 422/20 |
| 4,549,477 | A * | 10/1985 | McCabe, Jr. | 99/477 |
| 4,627,924 | A * | 12/1986 | Coste | 210/760 |
| 4,666,722 | A * | 5/1987 | Creed et al. | 426/393 |
| 4,827,727 | A * | 5/1989 | Caracciolo | 62/63 |
| 4,849,237 | A * | 7/1989 | Hurst | 426/332 |
| 4,933,411 | A * | 6/1990 | Gifford | 426/399 |
| 4,934,151 | A * | 6/1990 | Shima | 62/64 |
| 4,944,068 | A * | 7/1990 | Covell, III | 452/80 |
| 4,962,777 | A * | 10/1990 | Bell | 134/64 |
| 4,996,741 | A * | 3/1991 | Covell, III | 452/74 |
| 5,011,699 | A * | 4/1991 | Mitsuda et al. | 426/320 |
| 5,053,140 | A * | 10/1991 | Hurst | 210/704 |
| 5,054,292 | A * | 10/1991 | Klee | 62/63 |
| 5,087,466 | A * | 2/1992 | Coudrains et al. | 426/256 |
| RE33,852 | E * | 3/1992 | Gibot et al. | 62/52.1 |
| 5,173,190 | A * | 12/1992 | Picek | 210/651 |
| 5,184,471 | A * | 2/1993 | Losacco et al. | 62/63 |
| 5,227,184 | A * | 7/1993 | Hurst | 426/312 |
| 5,256,434 | A * | 10/1993 | Conway | 426/393 |
| 5,262,047 | A * | 11/1993 | Benskin et al. | 210/181 |
| 5,318,708 | A * | 6/1994 | Benskin et al. | 210/748.11 |
| 5,322,623 | A * | 6/1994 | Benskin et al. | 210/195.1 |
| 5,352,467 | A * | 10/1994 | Mitchell et al. | 426/316 |
| 5,447,640 | A * | 9/1995 | Omi et al. | 210/748.19 |
| 5,452,588 | A * | 9/1995 | Onodera | 62/381 |
| 5,484,332 | A * | 1/1996 | Leech et al. | 452/173 |
| 5,484,615 | A * | 1/1996 | Kounev | 426/238 |
| 5,667,829 | A * | 9/1997 | Herlig | 426/238 |
| 5,865,293 | A * | 2/1999 | Napadow | 198/495 |
| 5,879,732 | A * | 3/1999 | Caracciolo et al. | 426/231 |
| 5,910,420 | A * | 6/1999 | Tuompo et al. | 435/18 |
| 6,167,709 | B1 * | 1/2001 | Caracciolo et al. | 62/63 |
| 6,408,701 | B1 * | 6/2002 | Fujita | 73/864.71 |
| 6,551,182 | B2 * | 4/2003 | Caracciolo, Jr. | 452/81 |
| 6,803,066 | B2 * | 10/2004 | Traeder et al. | 426/333 |
| 6,908,636 | B2 * | 6/2005 | Howarth | 426/310 |
| 6,919,364 | B2 * | 7/2005 | Howarth et al. | 514/389 |
| 6,986,910 | B2 * | 1/2006 | Howarth | 426/310 |
| 7,083,510 | B2 * | 8/2006 | Caracciolo, Jr. | 452/81 |
| 7,086,407 | B2 * | 8/2006 | Lynn | 134/94.1 |
| 7,100,461 | B2 * | 9/2006 | Bradley et al. | 73/864.33 |
| 7,156,225 | B2 * | 1/2007 | Jacksier et al. | 206/6 |
| 7,172,782 | B2 * | 2/2007 | Howarth | 426/310 |
| 7,182,966 | B2 * | 2/2007 | Howarth | 426/310 |
| 7,207,879 | B2 * | 4/2007 | Kelly et al. | 452/77 |
| 7,229,667 | B2 * | 6/2007 | Jacksier et al. | 427/248.1 |
| 7,275,982 | B1 * | 10/2007 | Brandt et al. | 452/177 |
| 7,470,172 | B2 * | 12/2008 | Carracciolo, Jr. | 452/81 |
| 7,601,053 | B2 * | 10/2009 | Brandt et al. | 452/177 |
| 7,767,240 | B2 * | 8/2010 | Howarth | 426/310 |
| 7,794,841 | B2 * | 9/2010 | Benesch et al. | 428/432 |
| 7,799,150 | B2 * | 9/2010 | Jacksier et al. | 148/516 |
| 7,832,550 | B2 * | 11/2010 | Jacksier et al. | 206/0.6 |
| 7,837,806 | B2 * | 11/2010 | Benesch et al. | 148/279 |
| 7,850,790 | B2 * | 12/2010 | Jacksier et al. | 148/279 |
| 7,870,822 | B2 * | 1/2011 | Adams et al. | 99/516 |
| 7,901,276 | B2 * | 3/2011 | McNaughton et al. | 452/149 |
| 7,905,154 | B2 * | 3/2011 | Jones, Jr. | 73/864.81 |
| 7,914,365 | B2 * | 3/2011 | McNaughton et al. | 452/149 |

FOREIGN PATENT DOCUMENTS

| | | | | |
|---|---|---|---|---|
| EP | 1233267 | A | * | 8/2002 |
| FR | 2663509 | A | * | 12/1991 |
| JP | 2001061403 | A | * | 3/2001 |
| JP | 2001355957 | A1 | * | 12/2001 |
| WO | WO 9814066 | A1 | * | 4/1998 |
| WO | WO 0013009 | A1 | * | 3/2000 |

OTHER PUBLICATIONS

"Chapter 97—Food Regulation", Apr. 2003, Wisconsin State Law, pp. 1-22.*

James Giese, Electrinic Noses, Food Technology, Mar. 2000, 96-100, vol. 54—No. 3, Products & Technologies Labratory.

Comparing Odor Evaluation Technologies, InfoMetrix, 1999, 1-4, Infometrix Inc., Woodinville WA.

R.P. Manginell, Monolithically-Integrated MicroChemLab for Gas-Phase Chemical Analysis, Oct. 5-9, 2003, 1247-1250, 7th International Conference on Miniaturized . . . , California.

Candace Stuart, Small Tech Provides Some Answers to a Nation Questioning Its Safety, Smalltimes Big News in Small Tech., Sep. 11, 2002, 1-3, Small Times Media.

A Chemical Analysis Lab on a Chip, ChemLab, 1-2, Sandia National Laboratories, Livermore CA.

Sandia Seeks Commercialization Partners for Hand-Held Chemical Analysis and Detection System, ChemLab, Oct. 7, 2003, 1-2, Livermore CA.

Sue Vorenberg, MicroChemLab Finds Disease's Fingerprint.

Gayle Ehrenman, Shrinking the Lab Down, 2004, 1-13, The American Society of Mechanical Engineers.

Sandia's Lab on a Chip to Spot Chemical Clues, 1-3, Livermore CA.

* cited by examiner

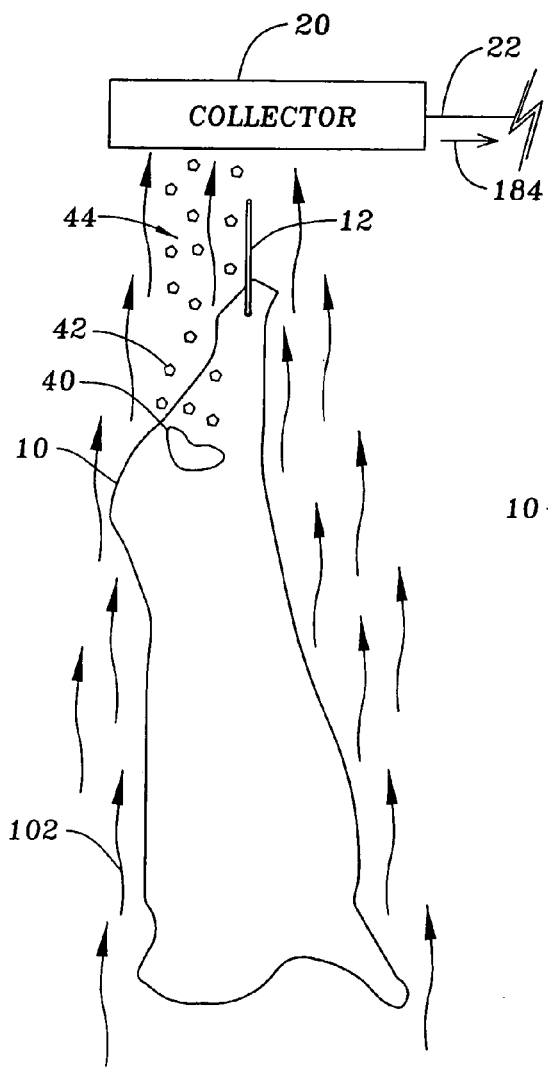
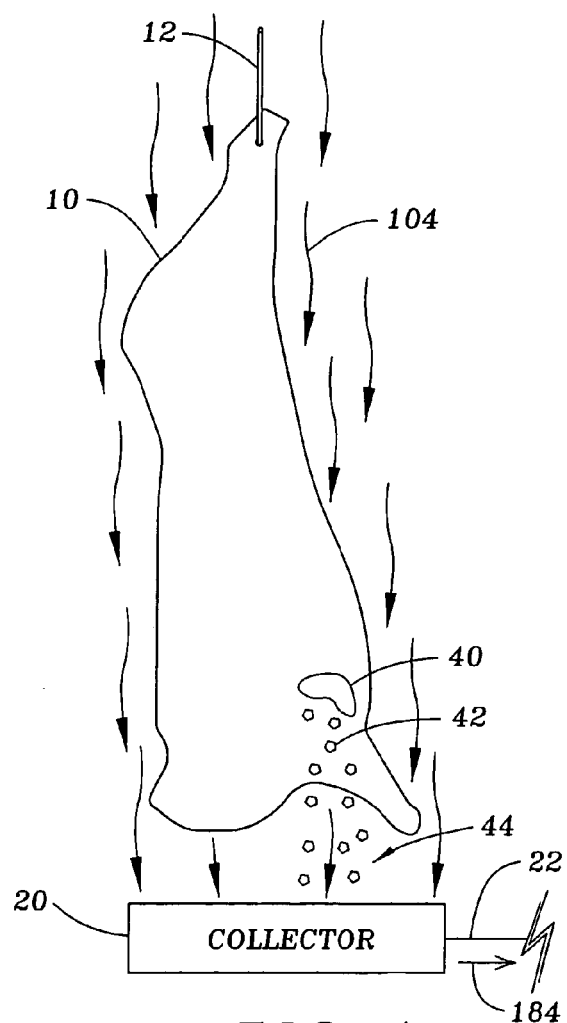
FIG. 3
FIG. 4

VIEW A-A

SECTION C-C

VIEW B-B

SECTION A-A

APPARATUS AND METHOD OF CONTAMINANT DETECTION FOR FOOD INDUSTRY

RELATED PROCEEDINGS

This application is a continuation of application Ser. No. 10/999,319 filed Nov. 29, 2004 now U.S. Pat. No. 7,905,154 and entitled "Apparatus and Method of Contaminant For Food Industry".

FIELD OF THE INVENTION

The present invention involves detection of contaminants such as bacteria and foreign chemicals on food. More particularly, it detects such contaminants in nano- to microscale, most typically in food production.

BRIEF DESCRIPTION OF THE DRAWINGS

FIG. 3 depicts an updraft and placement of the collector unit of the apparatus to utilize natural air flow;

FIG. 4 depicts a downdraft and placement of the collector unit of the apparatus to utilize natural air flow;

SUMMARY OF THE INVENTION

Figure 1:
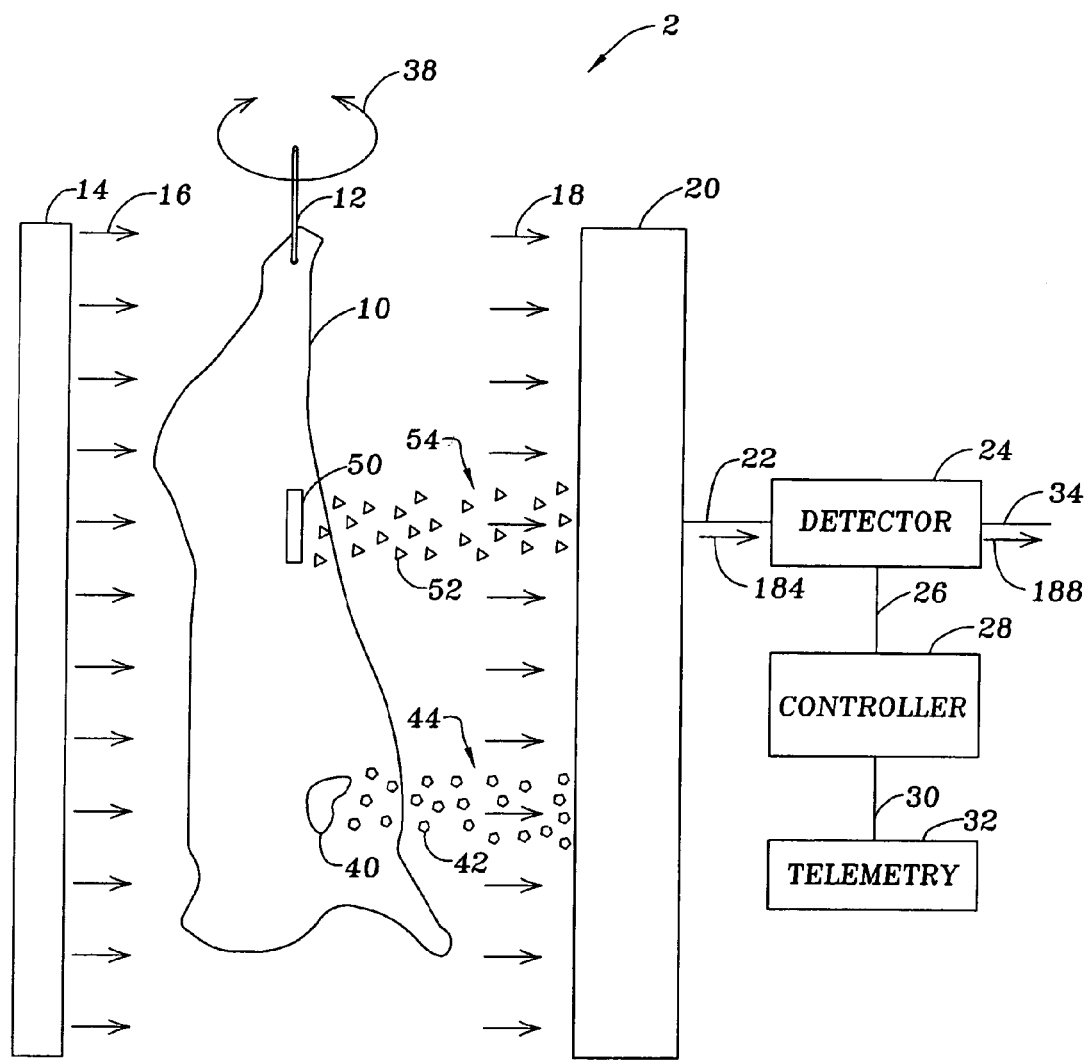
FIG. 1 is a generalized drawing of the method of the present invention, generally representing the components of the invention including an air handler, a collector, a detector, a controller, and telemetry.

The present invention is a method and apparatus for contaminant detection in the food industry. Particularly, the method and apparatus involve collecting air samples containing aerosolized contaminate particles from a foodstuff and analyzing the sample for presence of a contaminate. Aerosol lab-on-a-chip and/or electronic nose devices are utilized for the detection of contaminant particles More particularly, the invention includes a method for detecting contamination of foodstuffs including providing a foodstuff; collecting air surrounding the food stuff; and analyzing the collected air to determine the presence of contaminated particles. Additional steps may include creating airflow across a food stuff before collecting the air; providing an ALOC detector for analyzing collected air; and/or providing an electronic nose detector for analyzing collected air; utilizing an odor marker to mark identify the presence of food stuffs; and/or utilizing a contaminate marker to identify the presence of contaminated food stuffs.

The apparatus for detecting contamination of foodstuffs includes a collector unit; a detector unit in fluid connection with said collector unit; and a telemetry unit in electrical connection with said detector unit. A controller unit may be in electrical connection with the detector unit and/or with a telemetry unit.

The collector unit has a collecting surface with at least one air inlet, and optionally, at least one funnel-type device surrounding the air inlet. Multiple air inlets may be used. An air manifold may also be utilized to control flow to and from particular inlets.

An air handling unit may be disposed to create air flow across a foodstuff and into the collector. It may have at least one air nozzle disposed within a cavity of a foodstuff and/or within a food processing machine to allow passage of air through particulate food. It may be electronically controlled by said controlling unit. Also, a purge mechanism may be utilized.

The apparatus is a portable unit, including a hand held unit.

An odor marking unit and/or a contaminate marking unit may be used on the apparatus.

BACKGROUND OF THE INVENTION

The Centers for Disease Control and Prevention (CDC) estimates that approximately 76 million people suffer from foodborne illnesses and 5,000 die from these illnesses in the United States each year. While many foodborne illnesses may be caused by poor food handling and preparation, they may also be caused by eating contaminated or adulterated foods. To reduce the number of foodborne illnesses from contaminated and adulterated foods, manufacturers can recall food that poses a risk of illness or injury. The U.S. Department of Agriculture (USDA) and the Food and Drug Administration (PDA) documented more than 3,700 food recalls from the mid-1980s through 1999. The USDA identified 515 recalls of fresh and processed meat and poultry from calendar year 1984 through 1999. The FDA identified 3,248 recalls of other food from fiscal year 1986 through fiscal year 1999. The USDA and FDA indicate approximately 61 of these recalls were outbreaks of foodborne illnesses, and have identified at least five bacteria and two viruses responsible for the outbreaks: E.CO//0157: H7, *Staphyloccocus* species (toxin related), *Vibrio parahaemolyticus, Listeria monocytogenes, Salmonella* species, Hepatitis virus type A, Norwalk or Norwalk-like viruses. Foods involved in recalls vary widely, but some of the more common ones include oysters, ground beef, sprouts/seeds, strawberries/strawberry products, unpasteurized fruit juices/ciders, cold cuts hot dogs, chicken and pork.

The General Accounting Office (GAO) noted that food industry officials indicated recalls have a significant economic impact on affected companies through lost sales and food retrieval costs. The extent of the impact depends on such factors as the amount and value of the food recalled, its location in the distribution process, and the severity of the health risk. In addition, following a recall, consumers may stop buying a company's products or switch to another company's brand for future purchases. In some cases, this impact may lead to a company going out of business, particularly if the company is marginally profitable or already experiencing other problems. For example, a well-known company, Hudson Foods, went out of business after recalling approximately 25 million pounds of ground beef patties.

Recalls may also have an economic impact on companies other than the one conducting the recall. For example, according to the Food Marketing Institute, retail supermarkets may experience a drop in sales if consumers avoid the recalled food and other products by the same manufacturer or even other brands of the recalled item. In addition, companies that use a recalled product as an ingredient can incur significant costs from a recall. For example, if a particular brand of pepperoni is recalled a company using that brand in its frozen pizzas may have to recall the pizzas. Although the pizza manufacturer would be reimbursed for the lost revenues and replacement costs, it may also experience a drop in future sales if consumers have a negative impression of the pizza because of the recall. Because of them economic impact of recalls, many food companies have determined it necessary to carry "recall insurance" to cover lost revenues and retrieval costs, although many in the food industry have determined it cost prohibitive, leaving them open to the losses. G-40 *Report to Congressional Requesters "Food Safety: Actions Needed by the USDA and FDA to Ensure that Companies Promptly Carry Out Recalls"*, GAO/RCED-00-195, August 2000.

The food processing industry, in an effort to avoid such problems and reduce costs, carries out more than 144 million microbial tests costing five to ten dollars each. About twenty-four million of these tests are for detection of food pathogens based on biochemical profile analysis, immunogenic tests (such as enzyme linked immunosorbent assays or ELISA) and DNA/RNA probes. These tests are reliable, but most require two to seven days to complete because of the steps that are needed to resuscitate cells, increase cell numbers or amplify genetic material needed for detection. This time period is too long for real-time detection of contamination in a food plant and is sufficiently long for contaminated food to be formulated, processed, packaged, shipped, and purchased and eaten by the consumer. Current tests require at least several days to confirm presence of *Listeria monocytogenes*, for example. The number of annual tests is only expected to increase due to heightened consumer concerns about food safety and the requirement of compulsory testing.

In general, diagnostic tools typically used for detecting or quantitating biological analytes rely on ligand-specific binding between a ligand and a receptor. Ligand/receptor binding pairs used commonly in diagnostics include antigen-antibody, hormone-receptor, drug-receptor, cell surface antigen-lectin, biotin-avidin, substrate/enzyme, and complementary nucleic acid strands. The analyte to be detected may be either a member of the binding pair; alternatively, the analyte may be a ligand analog that competes with the ligand for binding to the complement receptor.

A variety of devices for detecting ligand receptor interactions are known. The most basic of these are purely chemical/enzymatic assays in which the presence or amount of analyte is detected by measuring or quantitating a detectable reaction product, such as a detectable marker or reporter molecule or ligand. Ligand/receptor interactions can also be detected and quantitated by radiolabel assays.

Quantitative binding assays of this type involve two separate components: a reaction substrate, e.g., a solid-phase test strip and a separate reader or detector device, such as a scintillation counter or spectrophotometer. The substrate is generally unsuited to multiple assays, or to miniaturization, or for handling multiple analyte assays. Further, these methods typically don't operate in "real time" situations.

In recent years, there has been a merger of microelectronics and biological sciences to develop what are called "biochips."

The term "biochip" has been used in various contexts but can be defined as a "microfabricated device that is used for delivery, processing, and analysis of biological species (molecules, cells, etc.)." Such devices have been used, among other things, for the direct interrogation of the electric properties and behavior of cells and optical detection of DNA hybridizations using fluorescence signals in the commercially available "DNA-chips". Prior art chips have used impedance spectroscopy or simple impedance to detect microorganismal presence. U.S. patent application to Gomez et al., Pub, No. 2003/0157587, Aug. 21, 2003. The Gomez et al. application, utilizes bioseparation techniques on a biochip to detect a microbiological entity. The Gomez et al. method however, requires utilization of fluid samples and, preferably, a purification process prior to injection of the fluid on the biochip. Additionally, these types of biochips are usually limited to a detection capability of one or two organisms per chip.

There is clearly a need in the art for faster contaminant detection capability to facilitate a quick, reliable answer to the food industry of the presence of contaminants at potentially multiple stages in the manufacturing or preparation process. Further, the process needs to be repeatably reliable. Additionally, it would be extremely desirable to avoid complicated processes such as preparing solutions of, for example, ground beef, in order to detect contaminants. Such solutions are only spot reliable and time consuming. Therefore, there is a great need in the art for a method and apparatus which will detect contaminants, preferably multiple types of contaminants, on food during the preparation process and potentially at multiple points in the preparation process, for the entire supply instead of for small samples, and without having to prepare a liquid solution of the food product.

DESCRIPTION OF A PREFERRED EMBODIMENT

The present invention comprises a novel detection apparatus and method for detection of contaminants in and on food products. More particularly, it involves use of a contaminant detector utilizing an aerosol lab-on-a-chip (ALOC) device or electronic nose device to chemically detect contaminants on food products by sampling the air surrounding the products.

For the purposes of this disclosure the following definitions shall apply:

Aerosol lab-on-a-chip (ALOC) is a device which integrates one or more of a variety of aerosol collection, classification, concentration (enrichment), and characterization processes onto a single substrate or layered stack of substrates; Contaminants are materials found in or on food products which are foreign to the product itself and may include, but are not limited to, chemicals, fecal material, dirt and other detritus, microbes, viruses, fungi and protozoa;

Electronic noses are devices which are used for automated detection of classification of odors, vapors and gases. They are comprised of a chemical sensing system and a pattern recognition system (artificial neural network).

Food products comprise any commonly known food stuff including raw or processed foods at any stage of production in any piecemeal or whole fashion. The preferred embodiment of the invention comprises a contaminant detection apparatus for use in the food industry, with particular usefulness to the meat industry. The detection method comprises providing a foodstuff for analysis, collecting aerosolized contaminant particles from air surrounding the foodstuff, and analyzing the air to detect the presence of contaminant. Optionally, the additional step of creating airflow across the foodstuff may be used before the collection step.

The contaminant detector of the invention comprises an aerosol collector in fluid connection with a detector. The detector may utilize an aerosol-lab-on-a-chip or an electronic nose device. The apparatus may additionally comprise a controller and/or telemetry devices in electrical and/or electronic connection with the detector. Optionally, the controller may be in electrical and/or electronic connection with an optional air handling unit which provides an air flow across a foodstuff which is to be evaluated. Further optionally, an odor marker may be utilized for detection which will alert the controller that a food stuff is in place. Also, contaminant markers may be utilized to mark a contaminated foodstuff to allow for non-batch level removals of contaminated foodstuffs. Finally, the apparatus may additionally utilize typical food industry food handling devices.

The preferred contaminant detector apparatus 2 of the invention, as shown depicted in FIG. 1, comprises placing the foodstuff 10 for testing, optionally in a hanging position on hook or other positioning device known in the art (e.g., hanger, holders, clamps) 12 in somewhat close proximity with aerosol collector 20, for allowing maximum beneficial airflow across carcass 10. The positioning device can rotate 38, preferably 360° as shown in FIG. 1. Preferably, the foodstuff is placed approximately five feet or less from the collector surface. More preferably, the foodstuff is placed approximately one foot or less from the collector. Air flow handling apparatus 14 may be optionally employed to create a sustained or varied air current 16 across meat 10, or ambient air 16 may be used. Naturally or mechanically aerosolized contaminant particles 42 will be moved by air current or ambient air 16 from carcass 10 and combined air current/aerosolized contaminant particles 18 will flow naturally (or in an assisted manner if forced air current 16 is applied) to aerosol collector 20. An assisted air flow is not required, but may be helpful in moving aerosolized contaminant particles or in providing the mechanical assist to aerosolize the particles from the surface of the food product. Aerosol collector 20 is maintained in fluid (gaseous) connection with detector 24. Detector 24 preferably comprises an aerosol lab-on-a-chip as described in U.S. Pat. No. 6,386,015 to Rader, et al. Detector 24 is preferably electrically connected to optional controller 28 which may include electrical devices known in the art for controlling air flow from handler 14 to provide a range of air flow rates, and may include sensors for detecting presence of foodstuffs particularly "odor markers", such as but not limited to the particular scent of blood to identify the presence of meat within the apparatus or identifiers of the foodstuff such as barcodes, smart tag codes which may be read by a corresponding RFID reader, or other identification methods known in the art. Controller 28 is electrically connected to telemetry 32 (or detector 24 is electrically connected thereto if controller 28 is not utilized). Detector 24 comprises an ALOC device as disclosed in Rader "015: a tool to collect, classify, concentrate, and/or characterize gas-borne particles. The basic principle underlying the ALOC is to take advantage of micromachining capabilities to integrate a variety of aerosol collection, classification, concentration (enrichment), and characterization processes into a single package which is compact, rugged, self-contained, and inexpensive to manufacture. Thus, a suite of discrete laboratory aerosol characterization techniques could be combined onto a single substrate, or stack of substrates, along with aerosol preconditioners and gas handling processes. The ALOC is analogous to the integrated circuit, wherein a variety of discrete electronic (aerosol) components are combined onto a single chip to build-up complex electrical (aerosol characterization) systems. The performance of several of these analytic aerosol characterization techniques would benefit by miniaturization (e.g., particularly the inertial techniques). By constructing arrays of identical parallel modules, it should be possible to reduce gas velocities that could give a quadratic reduction in pressure drop and consequently a quadratic reduction in power consumption. As pointed out above, sampling discrepancies would also be reduced; i.e., by virtue of their close proximity on the chip, each technique could be analyzing essentially the same sample. The performance of preconditioners, such as concentrators or size sorters, would also benefit by miniaturization, and could be built into layers above the diagnostics as needed. Gas-moving devices, such as pumps or fans, can be provided external to or fabricated onto the ALOC to provide the gas throughput needed for the aerosol sampling and analysis but are optional not essential. Electronic circuitry could also be fabricated onto the ALOC to provide for process control (valves, switches, etc.), signal processing, data analysis, and telemetry. Moreover, if the ALOC can be made sufficiently small and rugged, it could be placed directly into harsh (corrosive, high temperature, etc.) environments.

Figure 2:
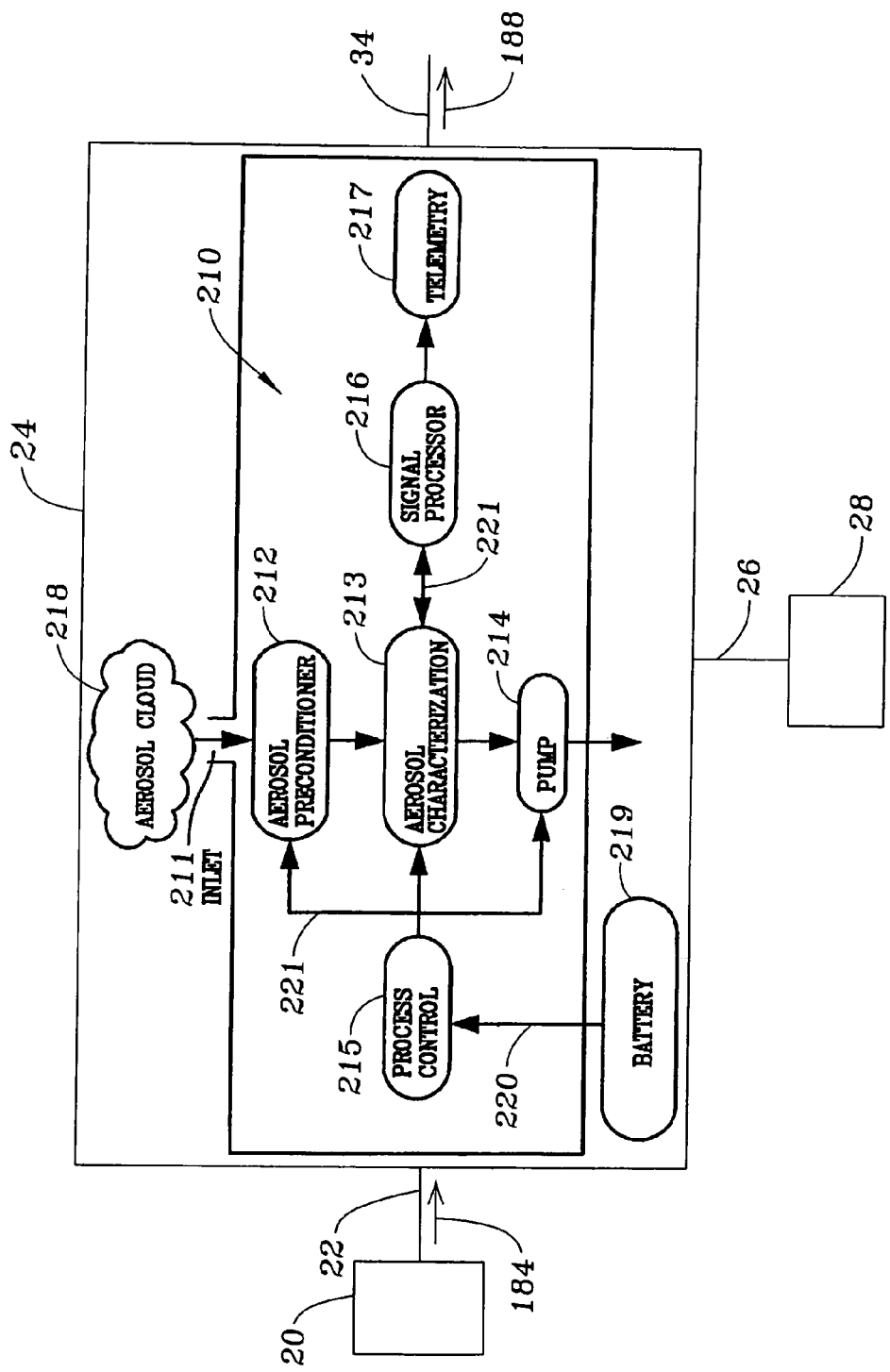
FIG. 2 is a box diagram of an aerosol lab-on-a-chip device.

A schematic of an embodiment of the ALOC is shown for a single aerosol characterization technique in FIG. 2. The device components in the flow path are formed on a substrate 210, and comprise an aerosol inlet 211, an aerosol condition (pre-conditioner) 212, an aerosol characterization module 213, and a gas moving means, or "pump", 214, necessary in the absence of a moving gas stream, to establish a gas flow through the aerosol characterization module(s) of sufficient volume and velocity to ensure that an adequate number of particles are sampled. Pump 214 may be provided external to substrate 210, or it may be fabricated onto substrate 210 (onboard configuration is shown in FIG. 1). Pre-conditioner 212 may or may not be needed depending on the application. Support components are also shown which provide an active process control 215, signal processing/data analysis (signal processor) 216, and telemetry 217. The aerosol inlet 211 is designed to receive gas-borne particles from an ambient aerosol cloud 218. Note that none, some, or all of the support components 215, 216, and 217 may be needed for a particular characterization technique. Any number of characterization modules (and support processes) may be combined in parallel or in series on a single-chip or stacked-chip ALOC; by combining characterization modules based on independent physical measurements, it would be possible to perform simultaneous analysis of a wide array of particle properties. In addition, construction of parallel arrays of identical devices (i.e., multiple copies of FIG. 2) on a single substrate would have the advantage of providing, increased overall device efficiency, signal enhancement, and in particular, increased operational flexibility. For example, an ALOC could be made to handle high total gas flow rates by assembling large numbers of individual devices operating at low flow rates (with lower pressure drops).

Finally, power for the device is provided by a standard low-voltage source, such as a battery 219, through a set of leads 220 connected to a data/power bus 221 located on the integrated chip. Power also may be supplied by a battery incorporated directly onto the ALOC substrate, or by any other means known to those skilled in the art.

The functions of the individual components are described briefly now. 1) The aerosol inlet must provide a path that admits the particle-laden gas into the ALOC assembly. The shape of the inlet must be designed carefully, as is well known in the prior art, so as to avoid particle inertial inlet losses and to provide a suitable gas inlet velocity profile, and to avoid large pressure drops. 2) The term aerosol condition is used hereinafter to describe any collection of processes that may be used to either classify, concentrate, or in some way manipulate an incoming stream of particles comprising an aerosol prior to those particles reaching a characterization module. As a classifier, the conditioner can be used to accept or reject particles above or below a desired size, or within a desired size range. As a concentrator, the conditioner can be used to preferentially increase the local concentration of particles in a desired size range. 3) The purpose of the aerosol characterization module is to provide a measurement of some physical property of the particle, including prior art such as techniques based on particle light including prior art such as techniques based on particle light scattering, inertial response, or electric mobility. Many of the in sit or extractive techniques discussed above would be suitable for miniaturization. A complete characterization of the aerosol would require a determination of the distribution of size, shape, and chemical, physical, and biological composition of the suspended particles comprising the aerosol. 4) A gas moving device may be necessary, in the absence of a moving gas stream, in order to establish a flow of a sufficient volume and velocity of gas, and therefore, an adequate number of particles, through the characterization module(s) in order to ensure an accurate measurement. The gas moving device can be any means capable of generating a pressure differential such as a mechanical pump, a sorp pump, a fan, or ion or diffusion pumps, and can be external to or fabricated onto the ALOC. 5) Active process control would include sensors, circuitry, and control devices on-board the ALOC that would collectively act to maintain critical process parameters within acceptable operating ranges. Lumped into this module are additional flow handling devices, such as channels and valves, which may be needed to distribute/direct the gas flow among the various characterization modules. 6) Circuitry could also be provided to allow on-board signal processing or data analysis that would be used to reduce raw physical measurements from the aerosol characterization module into useful form. As an example, a pulse-height analyzer could be used to determine the peak scattering intensity needed to size a particle based on its scattering profile while passing through an illumination source. Systems could also be envisioned that would collect single-particle data and reduce it to obtain size distribution functions. 7) Telemetry could be used to send the acquired data to a remote collection unit. 8) Power to the ALOC is supplied by a standard low-voltage source, such as by a battery, which could be either external to, or built onto, the ALOC substrate.

Alternately, the apparatus of the invention may utilize electronic nose technology as detector 24. The two main components of an electronic nose are the sensing system and the automated pattern recognition system. The sensing system can be an array of several different sensing elements (e.g., chemical sensors), where each element measures a different property of the sensed chemical, or it can be a single sensing device (e.g., spectrometer) that produces an array of measurements for each chemical, or it can be a combination. Each chemical vapor presented to the sensor array produces a signature or pattern characteristic of the vapor. By presenting many different chemicals to the sensor array, a database of signatures is built up. This database of labeled signatures is used to train the pattern recognition system. The goal of this training process is to configure the recognition system to produce unique classifications of each chemical so that an automated identification can be implemented.

The quantity and complexity of the data collected by sensors array can make conventional chemical analysis of data in an automated fashion difficult. One approach to chemical vapor identification is to build an array of sensors, where each sensor in the array is designed to respond to a specific chemical. With this approach, the number of unique sensors must be at least as great as the number of chemicals being monitored. It is both expensive and difficult to build highly selective chemical sensors.

Alternate embodiments of the apparatus of the invention may utilize natural air flows instead of or in addition to fans or pumps for directing aerosol particles into collector 20. FIG. 3 depicts a natural air flow resulting from carcass 10 having a higher temperature than its surrounding ambient air. Draft 102 crosses contaminant 40 on carcass 10 and combines with naturally aerosolized contaminant particles 42 to form combined contaminant particle/air stream 44 and carry combined contaminant particles 42 into collector 20. FIG. 4 depicts a natural air flow resulting from carcass 10 having a lower temperature than its surrounding ambient air. Draft 104 crosses contaminant 40 on carcass 10 and combines with naturally aerosolized contaminant particles 42 to form combined contaminant particle/air stream 44 and carry particles 42 into collector 20 for analysis by the detector.

Figure 5:
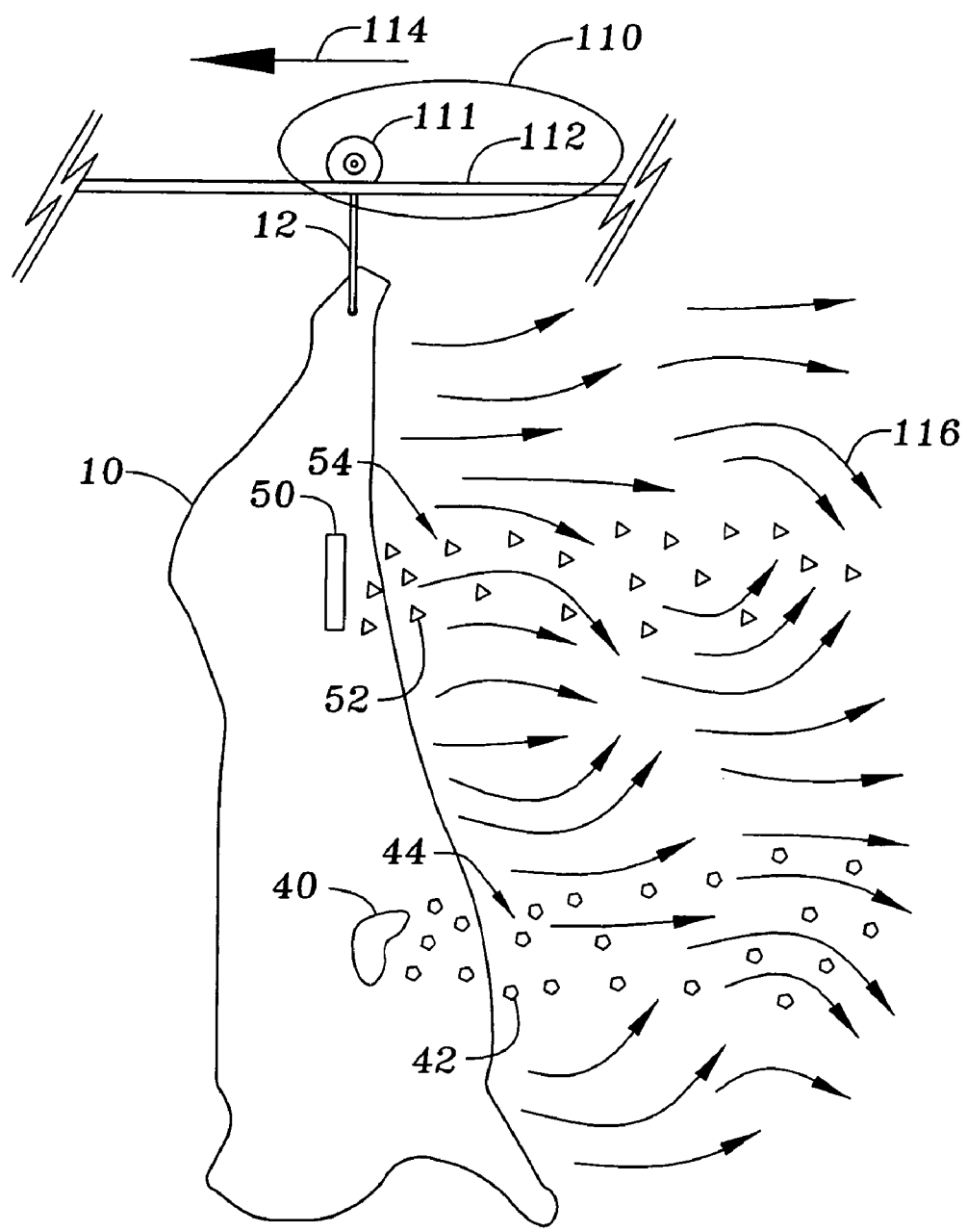
FIG. 5 depicts an air stream created by movement of a foodstuff and the aerosolized contaminate/particle air stream created.

The inventive apparatus may additionally comprise devices known in the art for movement of 25 foodstuffs, including but not limited to trolleys, conveyors, conveyor belts, buckets, grinders, packaging devices and extruders. FIG. 5 in particular depicts use of movement of foodstuff 10 to generate an air current. In the figure shown, meat 10 is hung by hook 12 to trolley wheel 111 of trolley 110. Trolley wheel 111 is rotated by an external force or gravity to convey meat 10 along trolley support rail 112 to a desired destination. As meat 10 is moved along trolley support rail 112, turbulent air flow 116 is create 30 by the movement of the meat through surrounding air.

Quality control devices may be utilized to ensure that the air flow is sufficient and directionally oriented to detect contaminants. In particular, odor markers 50 such as known chemicals sprayed or otherwise distributed onto the surface of a foodstuff 10 can be utilized to determine sufficient detection by prespraying foodstuffs and analyzing for the presence of the marker or alternately by spraying contaminated foodstuffs with odor markers after they have been determined to be contaminated, thereby allowing for disposal of only the contaminated foodstuffs instead of entire batch runs. Aerosolized particles 52 of odor marker 50 may be carried by combined air flow/contaminate particle stream 54 to a collector. Collectors may be placed in locations surrounding the path of travel of the meat to collect particles 42 aerosolized and combined with air flow to form combined contaminant particle/air stream 44.

Figure 6:
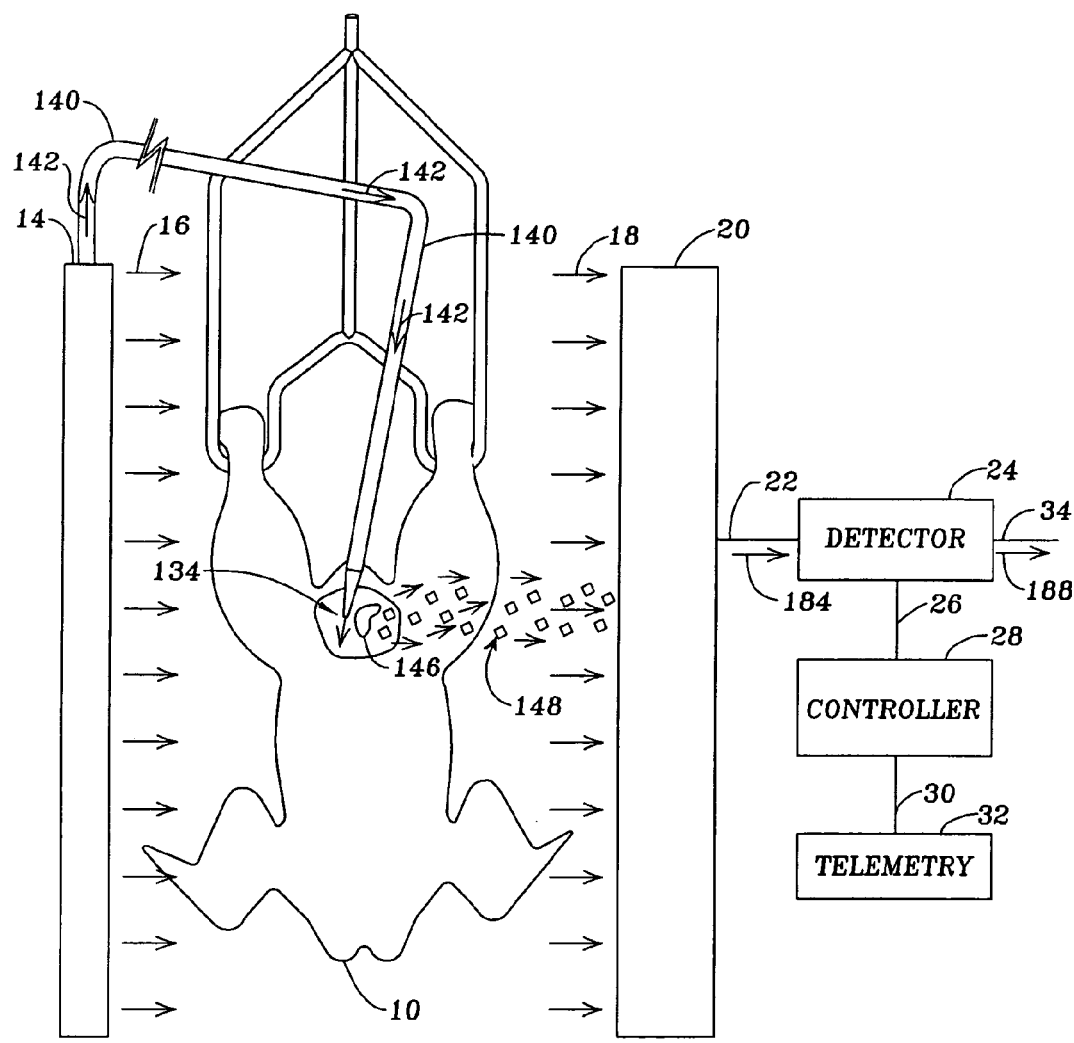
FIG. 6 depicts an air nozzle inserted into a body cavity of a foodstuff to detect contaminates.

Further, in the case of some types of foodstuffs, it may be beneficial to provide an embodiment for detecting contaminants within a cavity, for example, in the body cavity of poultry. FIG. 6 depicts an embodiment of the invention wherein air nozzle 140 is placed within a body cavity 134 of poultry. Air 142 flows from handler 14 through nozzle 140 and into cavity 134. Air stream 142 contacts a surface of body cavity 134 and is diverted away from the surface. In this flow, air stream 142 combines with aerosolized contaminant particles 146 to form combined contaminate particle/air stream 148. This combined particle/air stream 148 is then obtained by collector 20 for analysis. Meanwhile (or at another time during the processing procedure), air flow 16 flows across an outer surface of carcass 10 to obtain aerosolized particulates for analysis by collector 20.

Figure 7:
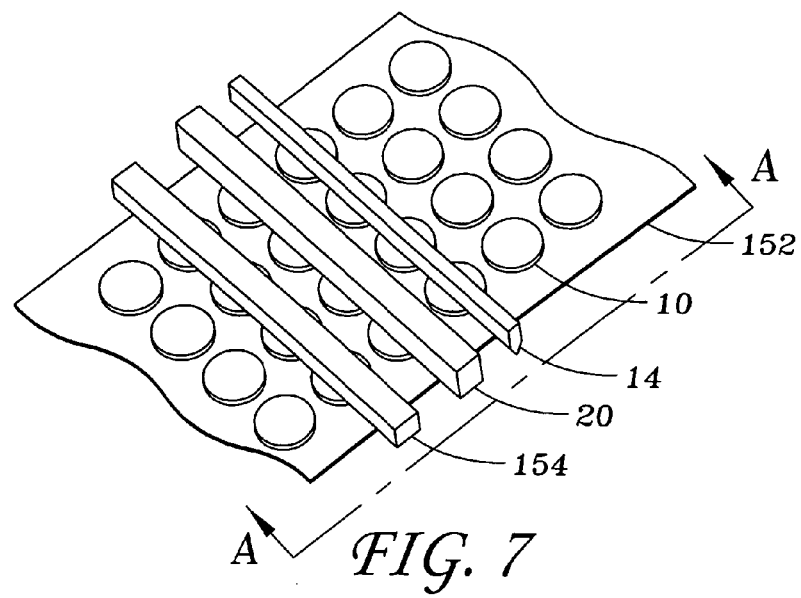
FIG. 7 depicts an embodiment of the apparatus adapted for use with a conveyor belt to detect contaminant on multiple items.
Figure 8:
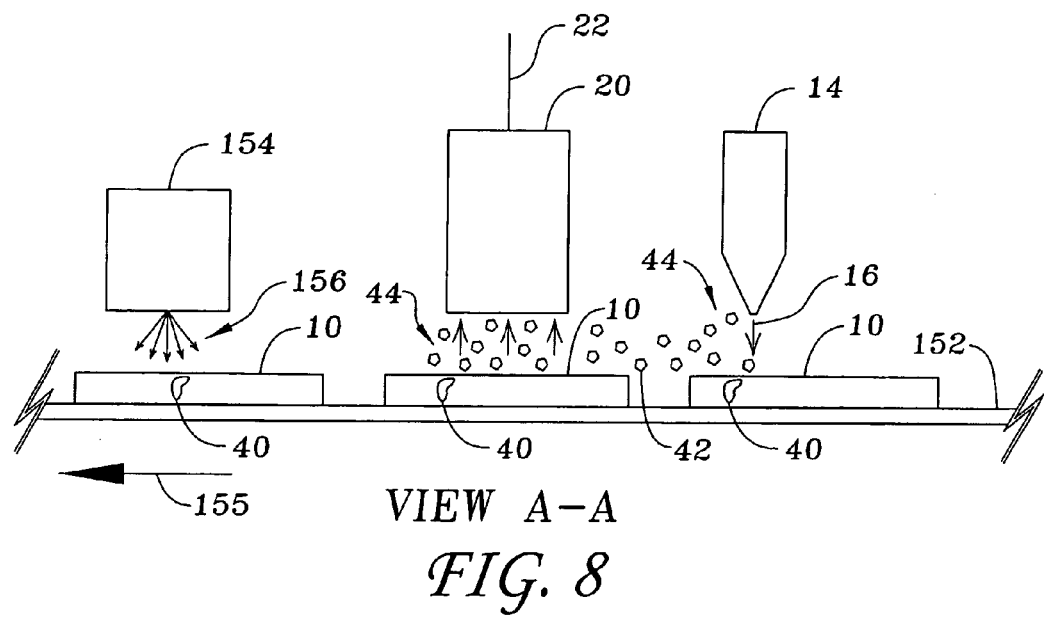
FIG. 8 depicts an embodiment of the apparatus with optional contaminant marker unit to identify contaminated areas/parts individually;"

FIGS. 7 and 8 depict an embodiment of the apparatus of the invention adapted for use with a conveyor assembly. Foodstuff 10, here depicted as hamburger patties, is disposed on an upper surface and conveyed along conveyor belt 152 in direction 155 to a desired destination. Air handler 14 is disposed to direct airflow across a surface of patties 10. Collector 20 is proximately disposed for receipt of deflected air from a surface of patties 10. Contaminate food marker 154 preferably comprises a General Regulated as Safe marker (GRAS) and is disposed to spray 156, stamp, or otherwise mark foodstuffs that are determined to have a contaminate to ensure removal of the contaminated food, and also to ensure that only the contaminated food must be disposed. Contaminate food markers may comprise other marking methods including but not limited to applying stickers to the foodstuff identified as contaminated.

Figure 9:
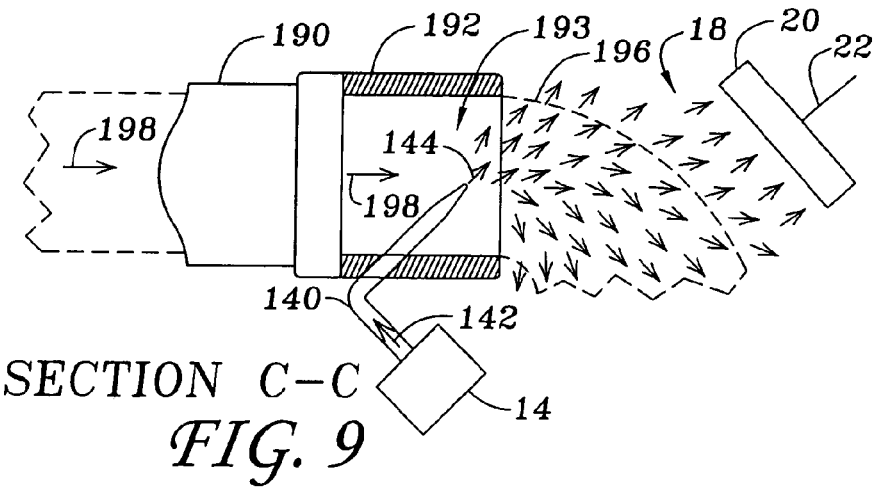
FIGS. 9-11 depict an output flange of a meat grinder and the use of an inserted nozzle to provide air through the particulate foodstuff for detection of contaminate.
Figure 10:
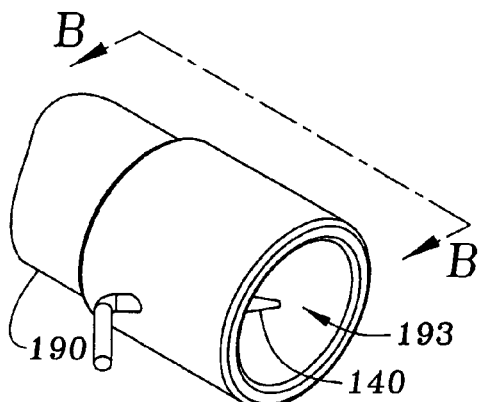
Figure 11:
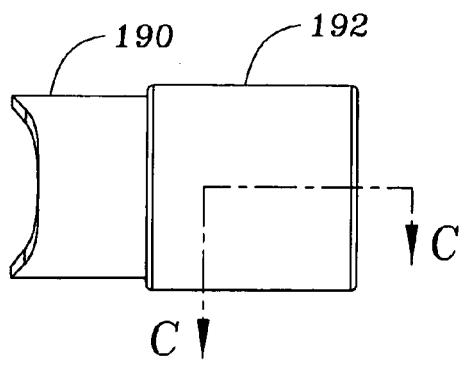

FIGS. 9, 10, and 11 are directed to utilization of the inventive apparatus as an embodiment adapted for a meat grinder or other foodstuff grinder, shredder, distributor. FIG. 9 shows output flange 190 of a meat grinder in use. Detector housing flange 192 is disposed at the outer edge of output flange 190. Air nozzle 140 is disposed into interior 193 of housing flange 192 and directs clean air 142 into interior 193. Foodstuff 10 flows through flange 190 in direction 198 and passes nozzle 140. Air flow 142 passes through ground foodstuff 10 and flows out of housing flange 192. Aerosolized contaminant particles combine with airflow 142 to form contaminant particle/air stream 18 which flows into collector 20 for analysis.

Figures 12, 13:
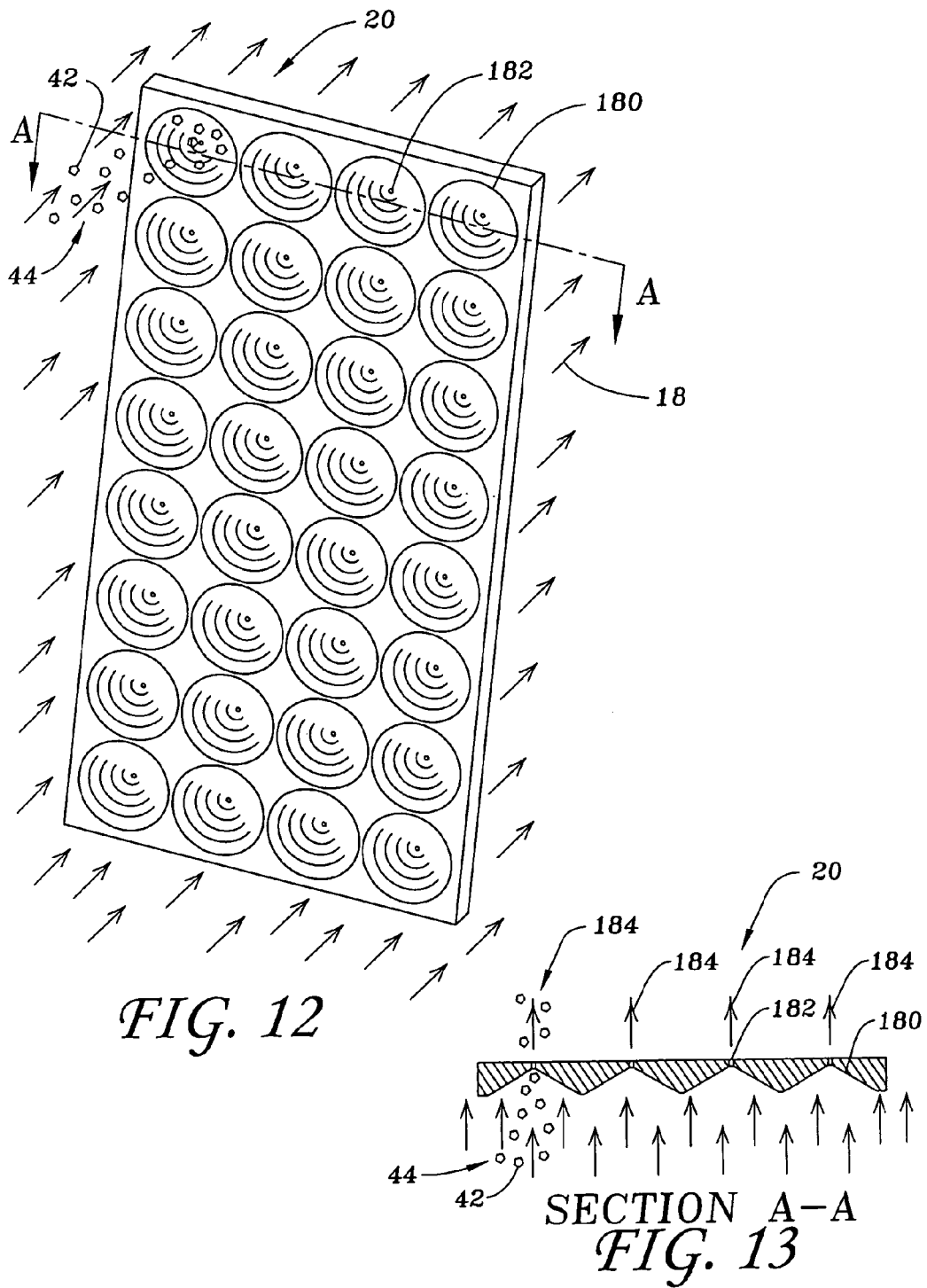
FIG. 12 depicts an air controller surface showing multiple air collection funnels leading to air inlets in gaseous fluid connection with the detection unit.
FIG. 13 depicts a cross-section of the center of a line of funnels as shown in FIG. 12, demonstrating contaminate particle/air stream flow through the air inlets.

FIG. 12 depicts an air receiving surface of collector 20, particularly depicting cone-shaped funnels 180 to aid with directing air flow to air inlet holes 182 of collector 20. The air receiving surface may have any surface configuration of inlet holes and/or funnels or otherwise configured openings to assist air collection. It should be noted that while flow-directing surfaces are preferable, they are not essential. A simple air inlet hole into collector would serve the purposes of the invention. Further, the number of inlets may be any number greater than or including one. The number of funnels/ducts/directional air devices may be any number greater than or including zero. The configuration shown may be altered to nonlinear patterns and may include any size and shape. However, it is beneficial to use a known pattern for the configuration of the collectors, since it may aid in determining exactly where the contaminant lies, therefore allowing only the contaminated foodstuff to be removed and preventing the waste of an entire batch run or carcass. This is easily comprehended. For example, if the collectors are placed, for instance, in a grid four inches apart and if a particular collector identifies contaminant, but the surrounding collectors do not, then it will be clear that the contaminant can be narrowed to at least the four inch radius surrounding the identifying collector. It is envisioned that this could be accomplished vertically and horizontally on a hanging foodstuff. It is also envisioned that detection may be assisted with rotation of the collectors or the foodstuffs in relation to the detectors since a positive reading would be checked by a series of readings.

FIG. 13 depicts a cross section of row of funnels 180 showing air flow of a combined contaminant particle/air stream with contaminant particles 42 through inlet holes 182 of funnels 180 and into tubing or ductwork 184 for transport of aerosol to detector 24 for analysis.

Figure 14:
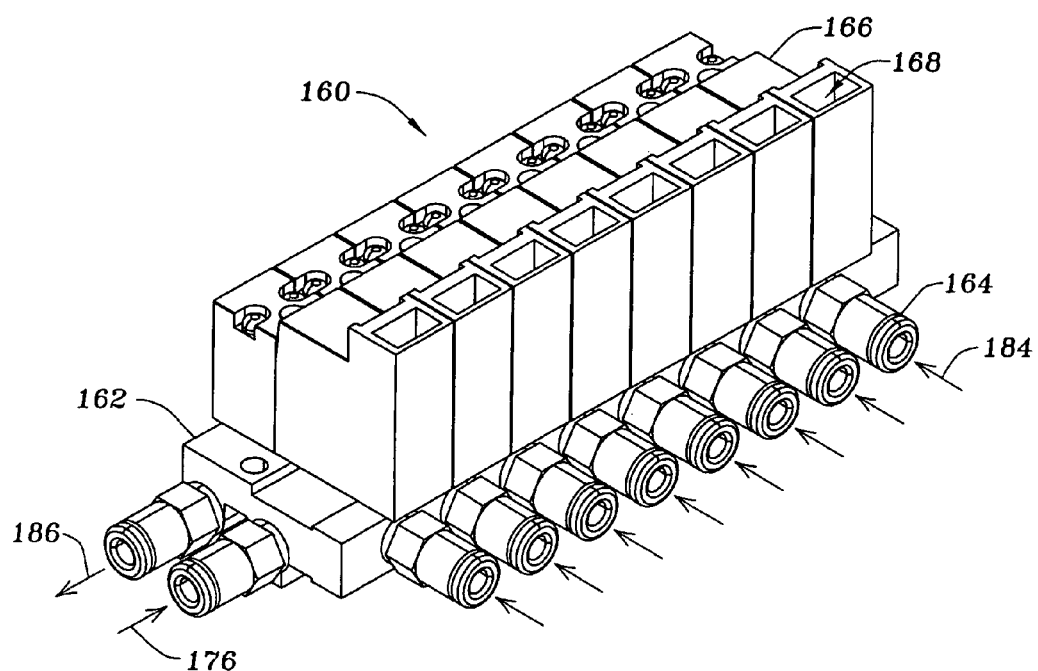
FIG. 14 depicts an air manifold for use in controlling air flow to each particular inlet.

FIG. 14 depicts an optional manifold assembly to direct airflow with use of multiple collections of contaminant particle/air streams. If more than one manifold assembly is used, the assemblies would be tied together pneumatically as is well-known in the art to result in only one air flow output 186. Collected air flows into manifold 160 through tubing 184 from air inlet holes of collector 20. The tubings 184 are fittingly connected to fittings 164 of manifold 160 and are directed into one or more manifolds 162. The manifolds contain solenoid valves 166 which can determine flow of the sample contaminant particle/air streams. The valves 166 may have electrical connections thereto as known in the art for manual or computerized control of the opening and closing of the respective valves. The use of a manifold assembly for the invention may be particularly important for quality control assurances. A faulty intake may be determined by individual testing each intake through a particular funnel (or system). Additionally, optional air purge 176 would allow a reverse air flow through the system to purge blockages in the tubing which may occur through use or cleaning. Air flow 186 comprises the resultant air flow of the manifold.

The device of the invention could easily be modified to be used in a handheld or otherwise portable device, and/or in conjunction with already existing detectors such as fluorescence, metal, plastic or other types of contaminant detectors or for any configuration necessary to accommodate the processing devices of the industry. The essentials for the operation of the device are air flow over a food surface into collectors for analysis. It is envisioned that many differing configurations will be utilized and the embodiments depicted herein are offered to be illustrative but not limiting of the invention.

The invention claimed is:

1. A method for detecting contamination of foodstuffs comprising:
   a) providing a foodstuff;
   b) activating an air blower to blow air across the foodstuff and into an aerosol collector; and
   c) analyzing the collected air to determine the presence of contaminated particles or gases.

2. The method of claim 1 further comprising blowing air into a cavity of the foodstuff.

3. The method of claim 1 further comprising
   a) placing an air controller across from the aerosol collector so that air passes from the air controller into the aerosol collector; and
   b) passing the foodstuff between the air controller and the aerosol collector.

4. The method of claim 3 further comprising rotating the foodstuff 360°.

5. The method of claim 1 further comprising the following step of providing an aerosol-lab-on-a-chip (ALOC) detector for analyzing collected air.

6. The method of claim 1 further comprising the following step of providing an electronic nose detector for analyzing collected air.

7. The method of claim 1 comprising the additional step of utilizing an aerosol contaminate marker to identify the presence of contaminated food stuffs.

8. The method of claim 7 further comprising the aerosol contaminate marker being detectible by an aerosol-lab-on-a-chip.

9. An apparatus for detecting contamination of foodstuffs comprising:
   a) an aerosol collector unit in a fixed position wherein a foodstuff is moved in proximity to the aerosol collector;
   b) a detector unit in fluid connection with said collector unit and having at least one detection component, wherein said detection component is capable of detecting contaminants to foodstuffs; and
   c) a telemetry unit in electrical connection with said detector unit.

10. The apparatus of claim 9 additionally comprising an air handling unit disposed to create air flow across a foodstuff and into said aerosol collector.

11. The apparatus of claim 9 additionally comprising an aerosol odor marking unit.

12. An apparatus for detecting contamination of foodstuffs comprising:

a) an aerosol collector unit;

b) a detector unit in fluid connection with said aerosol collector unit and having at least one detection component, wherein said detection component is capable of detecting contaminants to food stuffs;

c) a telemetry unit in electrical connection with said detector unit; and d) an air blower unit dimensioned to fit within a cavity of a foodstuff disposed to blow air across a foodstuff and into said aerosol collector.

13. The apparatus of claim 12 wherein said air blower unit is electronically controlled by said controlling unit.

14. The apparatus of claim 12 wherein said air blower unit is a portable unit.

15. The apparatus of claim 14 wherein said portable unit is a hand held unit dimensioned to fit within a cavity of a foodstuff.

16. A method for detecting contamination of foodstuffs comprising:

a) placing an aerosol collector unit in fluid communication with a detector unit;

b) placing a telemetry unit in electrical connection with said detector unit;

c) positioning an air handling unit disposed to create air flow across a foodstuff and into said aerosol collector unit;

d) blowing air into the cavity of the foodstuff with at least one nozzle of the air handling unit in proximity to the aerosol collector unit.

17. The apparatus of claim 16 wherein said air handling unit comprises at least one air blower nozzle dimensioned to fit within a cavity of a foodstuff.

18. A method for detecting contamination of foodstuffs comprising:

a) providing a foodstuff;

b) moving the foodstuff in proximity to an air collector wherein said collector unit additionally comprises multiple air inlets;

c) collecting air surrounding the foodstuff; and d) analyzing the collected air to determine the presence of contaminated particles.

19. The method of claim 18 for detecting contamination of foodstuffs comprising:

a) providing a collector unit; and b) placing the foodstuff at a temperature colder than the ambient air temperature where the collector unit is below the foodstuff.

20. The method of claim 18 for detecting contamination of foodstuffs further comprising:

a) providing a collector unit; and b) placing the foodstuff that is at a warmer temperature than the ambient air proximate to the collection unit and the collection unit is above the foodstuff.

* * * * *